United States Patent [19]

Züger

[11] Patent Number: 5,069,911
[45] Date of Patent: Dec. 3, 1991

[54] PHARMACEUTICAL 9,10-DIHYDROGENATED ERGOT ALKALOID CONTAINING COMPOSITIONS

[75] Inventor: Othmar Züger, Allschwil, Switzerland

[73] Assignee: Sandoz Ltd., Basel, Switzerland

[21] Appl. No.: 542,457

[22] Filed: Jun. 22, 1990

Related U.S. Application Data

[63] Continuation of Ser. No. 323,515, Mar. 14, 1989, abandoned, which is a continuation of Ser. No. 826,172, Feb. 5, 1986, abandoned.

[51] Int. Cl.$^5$ .................. A61K 9/26; A61K 9/52; A61K 31/48
[52] U.S. Cl. .................. 424/469; 424/468; 424/470; 514/249; 514/250
[58] Field of Search ............ 514/249, 250; 424/468, 424/469, 470

[56] References Cited

U.S. PATENT DOCUMENTS

| | | | |
|---|---|---|---|
| 3,557,287 | 1/1971 | Berde et al. | 514/250 |
| 3,887,705 | 6/1975 | Serre et al. | 514/250 |
| 3,896,228 | 7/1975 | Richardson | 514/250 |
| 4,083,949 | 4/1978 | Benedikt | 424/469 |
| 4,091,099 | 5/1978 | Fehr et al. | 514/250 |
| 4,122,177 | 10/1978 | Fehr | 514/250 |
| 4,124,712 | 11/1978 | Stotz et al. | 514/249 |
| 4,195,086 | 3/1980 | Fehr et al. | 514/250 |
| 4,225,065 | 9/1980 | Audibert | 514/250 |
| 4,229,451 | 10/1980 | Fehr et al. | 514/250 |
| 4,239,763 | 12/1980 | Milavec et al. | 514/250 |
| 4,251,529 | 2/1981 | Maurer et al. | 514/250 |
| 4,259,314 | 3/1981 | Lowey | 424/469 |
| 4,315,937 | 2/1982 | Maclay et al. | 514/250 |
| 4,389,393 | 6/1983 | Schor et al. | 424/469 |
| 4,411,882 | 10/1983 | Franz | 424/462 |
| 4,440,772 | 4/1984 | Ojordjevic et al. | 514/250 |
| 4,479,911 | 10/1984 | Fong | 424/497 |
| 4,777,033 | 10/1988 | Ikura et al. | 424/81 |
| 4,795,643 | 1/1989 | Seth | 424/456 |
| 4,828,836 | 5/1989 | Elger et al. | 424/499 |
| 4,834,985 | 5/1989 | Elger et al. | 424/469 |
| 4,933,105 | 6/1990 | Fong | 424/497 |
| 4,996,058 | 2/1991 | Sinnreich | 424/462 |

FOREIGN PATENT DOCUMENTS

| | | | |
|---|---|---|---|
| 3013059 | 10/1981 | Fed. Rep. of Germany | 514/250 |
| 106419 | 6/1984 | Japan | 514/250 |
| 1202885 | 8/1970 | United Kingdom | 514/250 |
| 2048671 | 12/1980 | United Kingdom | 514/250 |
| 2063670 | 6/1981 | United Kingdom | 514/250 |

Primary Examiner—Shep K. Rose
Attorney, Agent, or Firm—Gerald D. Sharkin; Robert S. Honor; Walter F. Jewell

[57] ABSTRACT

A controlled release formulation for oral administration comprising
a 9,10-dihydro ergot alkaloid,
a pharmaceutically acceptable hydrophilic swelling substance and
a pharmaceutically acceptable inert fatty material.

11 Claims, 1 Drawing Sheet

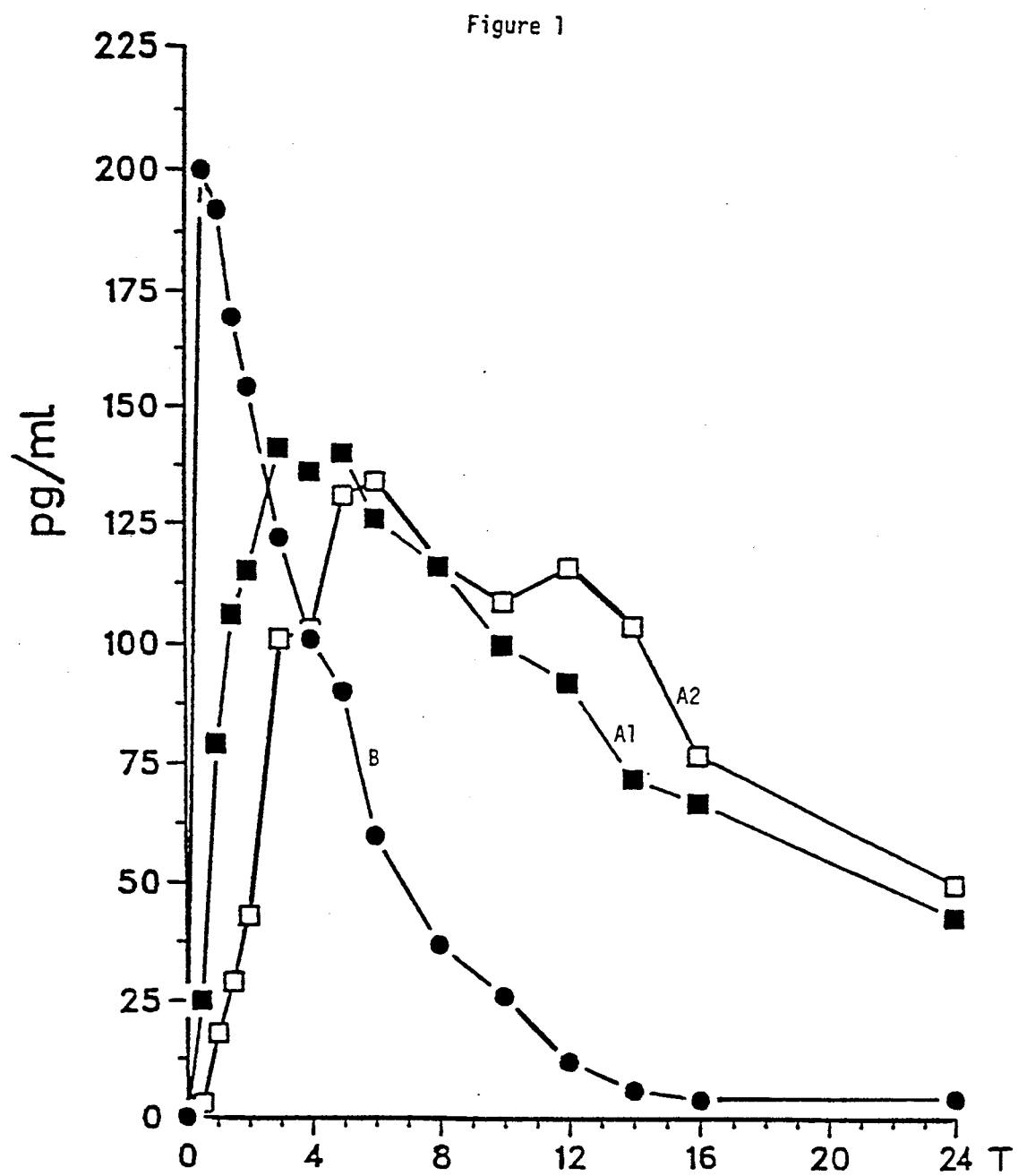

PHARMACEUTICAL 9,10-DIHYDROGENATED ERGOT ALKALOID CONTAINING COMPOSITIONS

This is a continuation application Ser. No. 323,515, filed Mar. 14, 1989, now abandoned, which in turn is a continuation division of application Ser. No. 826,172, filed Feb. 5, 1986, now abandoned.

This invention relates to pharmaceutical compositions containing 9,10-dihydro ergot alkaloids.

9,10-dihydro ergot alkaloids encompass the 9,10-dihydro-derivatives of natural ergot alkaloids as well as ergot alkaloids obtainable by fermentation or by chemical synthesis. They may e.g. have substituents, e.g. usually known in the chemistry of ergot alkaloids and may exist in the form of isomers, e.g. as 8R- and 8S-isomers, e.g. as described in "Ergot alkaloids and related compounds, Editors B. Berde and H. D. Schild, Springer Verlag, Berlin, Heidelberg, New York 1978, hereinafter referred to as Berde and Schild.

The most preferred compounds are dihydroergocornine, dihydroergocristine, dihydro-α-ergocryptine, dihydro-β-ergocryptine, and co-dergocrine and dihydroergotamine.

Co-dergocrine is the generic name of a molar 3:3:2:1 mixture of dihydroergocornine, dihydroergocristine, dihydro-α-ergocryptine and dihydro-β-ergocryptine, (see Berde and Schild, page 58).

For pharmaceutical use co-dergocrine may be used in the form of an acid addition salt, e.g. the ethane-sulphonate, the maleate, fumarate, tartrate, hydrochloride or preferably the mesulate. They exhibit the same order of activity as the free base form and are prepared in manner known per se.

The methanesulphonate salt is listed in the Merck Index, 1983, under the brand name HYDERGIN, see the reference 3596 on pages 526–527. This is also known as ergoloid mesylates.

The pharmacological and clinical properties have been extensively reviewed in the book of Berde and Schild.

Co-dergocrine modifies cerebral neurotransmission and improves impaired cerebral metabolic function. Furthermore, it has a stabilizing effect on the tonus of cranial vessels and has anti-hypertensive activity.

Co-dergocrine is therefore indicated for the treatment of cerebral insufficiency in the elderly and of cerebrovascular disorders, especially when associated with hypertension, as well as for the prevention of migraine.

Usual oral daily dosages are 3 to 6 mg. A recommended oral daily dosage is 4.5 mg, preferably divided into smaller dosages of 1.5 mg three times a day.

Dihydroergocornine, dihydroergocristine, dihydro-α-ergocryptine and dihydro-β-ergocryptine may be used individually for the same indications in the same dosage order.

The pharmacological and clinical properties of dihydroergotamine have been reviewed as well in Berde and Schild.

The compound may be administered in the form of the free base or of a pharmaceutically acceptable acid addition salt. Such acid addition salts are known. A typical acid addition salt form is the methanesulphonate salt (the mesylate), described in The Merck Index 1983, reference 3151, and sold under the brand name DIHYDERGOT.

Dihydroergotamine is indicated for use in the treatment of hypotension and orthostatic circulation disturbances, in the treatment of acute migraine attacks and related vascular headaches as well as in the interval treatment of migraine and other vascular headaches.

Further dihydroergotamine is indicated to be active in the treatment of Herpes Zoster.

The drug is usually orally administered in daily dosages of about 1–10 mg.

The present invention provides a controlled release formulation for oral administration comprising
  a 9,10-dihydro ergot alkaloid
  a pharmaceutically acceptable hydrophilic swelling substance and
  a pharmaceutically acceptable inert fatty material.

The invention especially provides such a controlled release formulation in which the 9,10-dihydro ergot alkaloid is a peptide alkaloid.

Hydrophilic swelling substances that are preferred include one or more natural, partially or totally synthetic, anionic or, preferably, nonionic hydrophilic gums, modified cellulose substances or protein aceous substances such as, for example, acacia, gum tragacanth, locust bean gum, guar gum, karaya gum, agar, peptin, carrageen, soluble and insoluble alginates, methylcellulose, hydroxypropylmethylcellulose, hydroxypropylcellulose, hydroxyethylcellulose, sodiumcarboxymethylcellulose, carboxypolymethylene, gelatin.

Preferred are cellulose hydrocolloids which include methyl cellulose, hydroxypropylcellulose and especially hydroxypropylmethylcellulose and sodium carboxymethylcellulose.

Suitable pharmaceutically acceptable inert fatty materials include beeswax; fatty acids; long chain fatty alcohols, such as, for example, cetyl alcohol, myristyl alcohol, stearyl alcohol, esters, e.g. glycerides such as glyceryl esters of fatty acids or hydrogenated aliphatic acids such as, for example, glyceryl mono-stearate, glyceryl distearate, glyceryl esters of hydrogenated castor oil and the like; oils such as mineral oil and the like. Fatty materials are preferably such with melting points between 30° and 90° C.

Most preferably fatty materials have a melting point from 45° C. to 65° C. and include glycerides such as glyceryl palmitates and stearates and fatty acids such as hydrogenated castor oil and fatty acid esters such as cetyl palmitate.

The formulation contains preferably both hydroxypropylmethylcellulose as a swelling agent and cetyl palmitate as a fatty material.

It is also convenient to incorporate in the formulation at least one of other soluble or insoluble pharmaceutical excipients such as calcium sulfate, calcium phosphate, lactose, mannitol, sucrose, sorbitol, colloidal silica, and magnesium stearate. Preferably a soluble excipient, especially lactose is present. The ratio of hydrocolloid to other excipient, may be e.g. from 1:0.5 to 1:2.

The formulation may be produced in conventional manner by mixing the ingredients together, preferably melting the fatty material. The resultant mixture is in powder form. The powder can be pressed to form a tablet, but is preferably filled into a capsule.

If the fatty material is melted, the drug and additional excipients such as lactose, silica, calcium sulphate or calcium phosphate may be taken up in the molten fatty material. The mixture is then allowed to solidify and is then divided into small particles (granules).

The resultant granulate may be mixed with a preferably porous, hydrophilic swelling substance and further excipients, e.g. magnesium stearate and the mixture may be pressed to form a tablet or may be preferably filled into a capsule.

In a preferred aspect the present invention accordingly provides a formulation containing a 9,10-dihydro ergot alkaloid in a fatty material matrix granulate, the granulate particles being in contact with a hydrophilic swelling substance.

Preferably the swelling substance is present in a porous form.

We have surprisingly found that the formulation possess an excellent stability, despite the fact that the alkaloids are sensitive to many chemical reagents. Moreover, the formulations have a satisfactory pharmacodynamic and pharmacokinetic profile.

The resultant retarded formulations in general have comparable bioavailability in standard clinical trials to conventional non-retarded formulations containing the same amounts of alkaloids. The formulations of the invention, even if administered once a day, may produce a therapeutic effect for at least 24 hours and even as much as 35 hours. The formulation may thus be administered only once a day in the known indications of the alkaloids at approximately the same daily doses as employed in the conventional non-retarded forms.

The 9,10-dihydro ergot alkaloids especially encompass 9,10-dihydro peptide ergot alkaloids of formula I

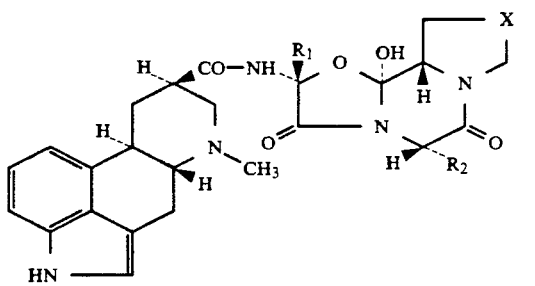

The groups $R_1$ and $R_2$ may be the same of different, e.g.
$R_1 = (C_{1-4})$alkyl, and
$R_2 = (C_{1-4})$alkyl, or benzyl, and
$X = CH_2$ or S.

9,10-dihydro ergot alkaloids encompass 9,10-dihydro peptide ergot alkaloids of formula I in which the carbon atom in position 9' is replaced by a sulfur atom, as disclosed in the British patent 2,109,795 B. The compounds may preferably be used in pharmaceutical form as acid addition salts.

The preferred compound of formula I wherein X=S is 9'-thia-9,10-dihydroergotamine. This is preferably used in the form of the hydrogen malonate. The preferred indication is for the prevention and treatment of vascular headaches and for the treatment of orthostatic syndrome. No publications on the clinical use of this active agent have been made and no specific sustained release forms of this agent have been described.

Epicryptine is the generic name of a compound of the formula I in which $R_1$=isopropyl, $R_2$=2R-butyl and $X=CH_2$, and is disclosed in the British patent 2,114,980 B. Its chemical name is: (5R,8R,10R)-N-[-(2R,5S,11S,12S)-5-(2R-butyl)-octahydro-12-hydroxy-2-isopropyl-3,6-dioxo-8H-oxazolo[3,2-a]pyrrolo[2,1-c]pyrazinyl]-6-methyl-ergoline-8-carboxylic acid amide. Epicryptine is also known as epicriptine.

The compound may be administered in the form of a pharmaceutically acceptable acid addition salt. Preferably the free base is used.

It is indicated for use in the treatment of lactation, galactorrhoea, hyperprolactinaemic hypogonadism, acromegaly or prolactinoma.

Epicryptine is also indicated for use in the treatment of cerebral insufficiency, e.g. for senile dementia, particularly the early forms thereof, and for increasing vigilance.

Additionally epicryptine is useful in the treatment of hypertonia, especially for geriatrics, and of stroke. The preferred indication is hypertension. The compound is administered at a daily dosage of from about 0.1 to 15 mg, preferably 2 to 5 mg.

The administration of the ergot alkaloids used according to the invention can occasionally be associated with adverse side effects, e.g. effects on the heart, vascular effects, central nervous system effects, autonomic and peripheral nervous system and endocrine effects. See Berde and Schild, pages 815–820.

We preferably keep the concentration of the ergot alkaloids on a therapeutically active level but between narrow limits and avoid the drug burst which may occur just after administration of non-controlled release preparations. This leads to temporary high blood levels and to proportionately strong adverse effects.

The formulations of the present invention are well tolerated.

Moreover, the present formulations provide similar profiles of activity in food interaction studies, e.g. before and after administration of breakfast, with fasted subjects.

The present invention especially provides controlled release formulations for oral administration containing co-dergocrine, dihydroergotamine or epicryptine as active agents in unit dosage forms.

The pharmaceutical formulations according to the invention, contain preferably 1 to 15 mg of 9,10-dihydro ergot alkaloid.

Preferred ratios of 9,10-dihydro ergot alkaloid to swelling substance are from about 1:4 to 1:50, e.g. 1:4 to 1:25.

Preferred ratios of 9,10-dihydro ergot alkaloid to fatty material are from 1:0.5 to 1:10.

Preferred amounts of co-dergocrine in unit dosage form are from 2 to 10 mg, especially 3-6, e.g. 4.5 or 3 mg. Preferably co-dergocrine is in mesylate form.

Preferably the ratio of co-dergocrine to swelling substance is from 1:50 to 1:10, especially from 1:10 to 1:30, e.g. from 1:15 to 1:25.

The ratio of co-dergocrine to the fatty material is preferably from 1:1 to 1:10, especially from 1:1 to 1:5.

If other excipients like lactose or magnesium stearate are present, then preferably the weight ratio of co-dergocrine to the other excipients is conveniently from 1:5 to 1:40, especially 1:15 to 1:40.

Preferred amounts of dihydroergotamine in unit dosage form are from 4-15 mg, e.g. 5 mg, especially 8-12, e.g. 10 or 7.5 mg. Preferably dihydroergotamine is in mesylate form as well.

Preferably the ratio of dihydroergotamine to swelling substance is from 1:4 to 1:20, e.g. 1:5 to 1:20, especially from 1:4 to 1:12 e.g. from 1:5 to 1:12.

The ratio of dihydroergotamine to the fatty material is preferably from 1:0.5 to 1:2, especially from 1:0.5 to 1:1.5 e.g. from 1:0.8 to 1:1.5.

If other excipients like lactose, silicon dioxide, magnesium stearate or tartaric acid, are present, then preferably the weight ratio of dihydroergotamine to the other excipients is conveniently from 1:3 to 1:20, especially from 1:4 to 1:15.

Epicryptine may also be present as an acid addition salt, but the preferred form in the controlled release formulation is the free base.

The unit dosage form contains preferably an amount of 2 to 7 mg, especially 5 mg of drug.

The present invention provides for the first time an oral pharmaceutical formulation containing 9'-thia-9,10-dihydroergocryptine or epicryptine for once-a-day administration. Once-a-day formulations may be formulated in conventional manner, e.g. to be a capsule or tablet and may contain from 1 to 15 mg of active agent. Preferably they have the same release profile as determined by in vivo or in vitro dissolution tests as for the formulations of the present invention, e.g. a release of about 50 to 90, e.g. 50 to 60, 70 to 80 or 80 to 90 per cent over 7 hours at 0.1 NHCl, e.g. as in the experimental conditions in Example 2.

In the following examples all temperatures are in degrees Centigrade and are uncorrected.

Further information on the proporties etc. of the pharmaceutical excipients named hereinafter may be obtained from the manufacturer, listed hereinafter, manufacturer's brochures or other sources, especially H. P. Fiedler Lexikon der Hilfsstoffe für Pharmazie, Kosmetik und angrenzende Gebiete, 2nd Edition 1981, Edito Cantor, Aulendorf, W. Germany.

Silicon dioxide (silica) is e.g. brand Aeorsil 200 available from Deutsche-Gold und Silberscheideanstalt, Frankfurt, W. Germany.

Glycerol ditripalmitostearat is e.g. brand Precirol Ato 5 available from ETS Gattefossé 929100 Boulogne-Brillancourt, France.

Hydroxypropylmethylcellulose 15000 cps and 4000 cps are e.g. brands Methocel K15M and Methocel 4EM available from Dow Chemical Company, Michigan 48640 U.S.A.

Cethyl palmitate is e.g. brand Cutina CPA available from Henkel 4000, Düsseldorf, W. Germany, or is available from Gattefossé or from A/S Johan C. Martens and Company, Bergen, Norway.

EXAMPLE 1

Composition of each capsule

| Ingredient | mg |
| --- | --- |
| a) Co-dergocrine (in mesylate form) | 4.5 |
| b) Lactose (200 mesh) | 124.265 |
| c) Silicon dioxide | 10 |
| d) Glycerol ditripalmitostearate | 40 |
| e) Hydroxypropylmethylcellulose 4000 cps | 110 |
| Capsule (Hard gelatine) | 78 |

Preparation (Charge of 6000 capsules)

Ingredients a), b) and c) are sieved and mixed. Ingredient d) is melted by heating to 56° C. (m.p. 54° C.) and is added to the mixture which is heated to 55° C. The mass is stirred for 2 minutes or until it is a homogenous mixture and cooled overnight. The cooled mass is broken up and sieved (through 250 micron openings). Ingredient e) is sieved (through 360 micron openings) and mixed in over 10 minutes. The mixture is then encapsulated.

EXAMPLE 2 TO 5

| Composition of each capsule Ingredient | Ex. 2 mg | Ex. 3 mg | Ex. 4 mg | Ex. 5 mg |
| --- | --- | --- | --- | --- |
| a) Co-dergocrine in mesylate form | 4.5 | 4.5 | 3.0 | 3.0 |
| b) Lactose (200 mesh) | 165.5 | | | |
| c) Cetyl palmitate | 10.0 | 8.0 | 8.0 | 8.0 |
| d1) Hydroxypropylmethyl-cellullose (15000 cps) | 90.0 | 70.0 | 70.0 | |
| d2) Hydroxypropylmethyl-cellulose (4000 cps) | | | | 90.0 |
| e) Magnesium stearate | | | 1.0 | 1.0 |
| Capsule (Hard gelatine; 78 mg) | | | | |

Preparation

The ingredients are mixed in analogous manner to that disclosed in Example 1, except that constituent d) is replaced by an equivalent amount of cetyl palmitate, the silicon dioxide c) is omitted and the hydroxypropylmethylcellulose d) is mixed with magnesium stearate.

In vitro release

In in vitro experiments (USP XXI, pages 1243–1244, Apparatus 1, 1000 ml 0.1n HCl, 100 rotations per min.) the following release results were obtained:

| | Release of co-dergocrine | | | Release of co-dergocrine | |
| --- | --- | --- | --- | --- | --- |
| Time (hours) | Ex. 2 | Ex. 3 | Time (hours) | Ex. 4 | Ex. 5 |
| 1 | 15% | 16% | 1 | 19% | 20% |
| 3 | 32 | 37 | 2 | 32 | 37 |
| 5 | 50 | 52 | 4 | 48 | 49 |
| 7 | 66 | 64 | 7 | 67 | 73 |
| 24 | 99 | 86 | 24 | 100 | 101 |

EXAMPLE 6

Composition of each capsule

| Ingredient | mg |
| --- | --- |
| a) Dihydroergotamine (in mesylate form) | 10.0 |
| b) Lactose (200 mesh) | 88.0 |
| c) Silicon dioxide | 1.0 |
| d) Glycerol ditripalmitostearate | 10.0 |
| e) Hydroxypropylmethylcellulose 4000 cps | 90.0 |
| f) Magnesium stearate | 1.0 |
| Capsule (Hard gelatine) | 62.0 |

Preparation (Charge of 6000 capsules)

Ingredients a), b) and c) are sieved and mixed. Ingredient d) is melted by heating to 56° C. (m.p. 54° C.) and is added to the mixture which is heated to 55° C. The mass is stirred for 2 minutes or until it is homogenous mixture and cooled overnight. The cooled mass is broken up and sieved (through 800 micron openings). Ingredients e) and f) are sieved (through 500 micron openings) and mixed over 10 minutes. The mixture is then encapsulated.

| In vitro release (Experimental conditions: see Example 2) | |
| --- | --- |
| Time (hours) | Release of dihydroergotamine (%) |
| 1 | 9 |
| 2 | 17 |
| 4 | 29 |
| 6 | 41 |

-continued

| In vitro release (Experimental conditions: see Example 2) | |
|---|---|
| Time (hours) | Release of dihydroergotamine (%) |
| 24 | 96 |

EXAMPLE 7

Composition of each capsule

| Ingredient | mg |
|---|---|
| a) Dihydroergotamine in mesylate form | 10.0 |
| b) Lactose (200 mesh) | 107.0 |
| c) Cetyl palmitate | 10.0 |
| d) Hydroxypropylmethylcellulose (15000 cps) | 70.0 |
| e) Silicon dioxide | 1.0 |
| f) Magnesium stearate | 2.0 |
| Capsule (Hard gelatine) | 62.0 |

Preparation

The ingredients are mixed in analogous manner to that disclosed in Example 6, except that constituent d) is replaced by an equivalent amount of cetyl palmitate.

| In vitro release (Experimental conditions: see Example 2) | |
|---|---|
| Time (hours) | Release of dihydroergotamine (%) |
| 1 | 24 |
| 2 | 41 |
| 4 | 65 |
| 6 | 80 |
| 8 | 100 |

EXAMPLE 8 TO 10

| Composition of each capsule Ingredient | Ex. 8 mg | Ex. 9 mg | Ex. 10 mg |
|---|---|---|---|
| a) Dihydroergotamine in mesylate form | 7.5 | 7.5 | 7.5 |
| b) Tartaric acid | 0.18 | 0.2 | 0.18 |
| c) Lactose | 81.32 | 144.3 | 81.32 |
| d) Cetyl palmitate | 8.0 | 5.0 | 8.0 |
| e) Hydroxypropylmethylcellulose (4000 cps) | 80.0 | 40.0 | 80.0 |

The ingredients are mixed in analogous manner to that disclosed in Example 6:

Constituents a), b) and c) are occluded in constituent d), the solidified mixture is granulated and is mixed with constituent e).

In vitro release (Experimental conditions: see Example 2)

| | Release of dihydroergotamine | | |
|---|---|---|---|
| Time (hours) | Ex. 8 | Ex. 9 | Ex. 10 |
| 1 | 10% | 14% | 10% |
| 2 | 19 | 26 | 22 |
| 4 | 33 | 49 | 41 |
| 6 | 46 | 67 | 56 |
| 24 | 96 | 99 | 101 |

Comparative clinical test

Objective: To study in healthy volunteers the bioavailability of co-dergocrine in an oral controlled release capsule A according to Example 2 in comparison to co-dergocrine in a conventional table B.

| Conventional composition in tablet form | |
|---|---|
| Ingredient | mg |
| 1. Co-dergocrine in mesylate form | 1.0 |
| 2. Stearic acid | 2.0 |
| 3. Talc | 4.0 |
| 4. Polyvinylpyrrolidone | 4.0 |
| 5. Starch | 8.0 |
| 6. Lactose | 141.0 |

The ingredients 1 to 6 were mixed together, granulated with a mixture of alcohol and water, dried and compressed to a tablet.

One dosage of two 4.5 mg co-dergocrine mesylate containing capsules A (=9 mg) was compared with one dosage of 4 conventional tablets B containing 1 mg co-dergocrine mesylate (=4 mg). The lower dose for the tablet was chosen to avoid expected side effects due to the high peak levels of the conventional non-controlled release tablets.

The study design was an open label, 2 period design with each subject randomly assigned to one of two treatment sequences, followed by a third treatment period in which all subjects received the identical third treatment. 10 healthy male volunteers received on a fasted stomach both treatments in the first hour periods, followed by one dosage of retard capsules A with food in period three.

Blood samples were obtained from the 10 volunteers by an indwelling cannula, at specific time points up to 24 hours after administration of the capsules.

BRIEF DESCRIPTION OF THE DRAWING

The co-dergocrine concentrations, measured after the administration of capsules A and tablet B, were plotted graphically as shown in accompanying in FIG. 1 as corresponding mean curves A.1 (without food), A.2 (with food) and B (without food) in picograms ml, time T in hours).

From the measured co-dergocrine concentrations, the following parameters were obtained (as arithmetic means).

| | Retard Caps.A with food | Retard Caps.A without food | Oral tablet B without food |
|---|---|---|---|
| AUC (Area under the curve, 0–24 hours) | 2066 | 2066 | 2242* |
| Peak (in picogram/ml) | 172 | 162 | 511* |
| Time (in hours) | 5.9 | 3.9 | 0.9 |

*Extrapolated from 4 mg to 9 mg

This is justified since co-dergocrine mesylate shows linear dose proportionality for the AUC in the 0–9 mg dose range.

The retard capsule A showed an AUC, similar to that of the conventional tablet B (corrected for the dose) when given on an empty stomach or with a meal. Compared to the tablet B the retard capsule A showed a statistically significant lower peak level and a delayed time to peak (from less than 1 hour to 3.9 h on a fasted stomach or 5.9 h when given with a meal). In general, however, the profile of compound A when given on a fasted stomach was similar to that when given after a meal, except for the delay in the absorption of drug with a full stomach (presumably due to a delay in stomach emptying).

The retard capsule A, given on a fasted stomach or with a meal, provides sustained release of drug without dose dumping and, which is especially noteworthy, without significant loss of bioavailability, compared to the oral tablet reference Standard B.

Side effects such as headache and gastrointestinal upset were transitory and were mild to moderate in severity.

Single dose of retard capsules A, administered as 2×4.5 mg retard capsules A are safe and well tolerated.

EXAMPLE 11

The co-dergocrine and dihydroergotamine in the above examples may be replaced by an equivalent amount of epicryptine or 9'-thia-9,10-dihydroergotamine.

What we claim is:

1. A controlled release formulation for oral administration comprising a 9,10-dihydro ergot of the formula

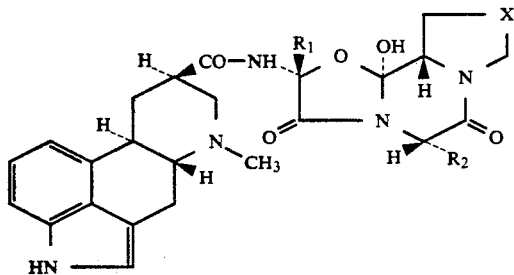

wherein
R₁ and R₂ may be the same of different,
R₁ is (C₁₋₄)alkyl, and
R₂ is (C₁₋₄)alkyl, or benzyl, and
X is CH₂
as a drug compound selected from the group consisting of, dihydroergoncornine, dihydroergocristine, dihydro-α-ergocryptine, dihydro-β-ergocryptine, co-dergocrine, dihydroergotamine,
epicryptine and acid addition salts thereof a pharmaceutically acceptable inert fatty material, in a weight ratio of drug compound to fatty material of 1:0.5 to 1:10 and selected from the group consisting of beeswax, fatty acids, fatty acid esters, long chain fatty alcohols and oils in the form of granule particles, the granulate particles being enveloped with dry particles of a pharmaceutically acceptable hydrophilic swellable substance in a weight ratio of drug compound to swellable substance of 1:4 to 1:50, the swellable substance selected from the group consisting of, natural or synthetic anionic or nonionic hydrophilic gums, modified cellulose and proteinaceous substances.

2. A formulation according to claim 1, wherein the drug is co-dergocine.

3. A formulation according to claim 1 wherein the swellable substance is hydroxypropylmethylcellulose.

4. A formulation according to claim 1 wherein the fatty material is a fatty acid ester.

5. A formulation according to claim 1 containing 1 to 15 mg of drug compound per unit dosage form.

6. A formulation according to claim 1, wherein the weight ratio of co-dergocrine to the swelling substance is from 1:10 to 1:50.

7. A formulation according to claim 1, wherein the drug compound is dihydroergotamine and the weight ratio of dihydroergotamine to the swelling substance is from 1:4 to 1:20.

8. A formulation according to claims 2 and 6, wherein the weight ratio of co-dergocrine to the fatty material is from 1:1 to 1:10.

9. A formulation according to claims 1 and 7, wherein the drug is dihydroergotamine and the weight ratio of dihydroergotamine to the fatty material is from 1:0.5 to 1:2.

10. A method for treating cerebral insufficiency and disorder, hypertension or migraine, which comprises administering a therapeutically effective amount of a formulation of claims 2, 6 and 8 to a subject in need of such treatment.

11. A method for treating hypotension, orthostatic circulation disturbances or migraine which comprises administering a therapeutically effective amount of a dihydroergotamine containing formulation of claims 1, 7 and 9 to a subject in need of such treatment.

* * * * *